United States Patent [19]

Mayer et al.

[11] Patent Number: 5,403,464
[45] Date of Patent: Apr. 4, 1995

[54] HIGH PERMEABILITY RATE OXYGEN SENSOR

[75] Inventors: William N. Mayer, White Bear Lake; Stephen D. Tuomela, Fridley, both of Minn.

[73] Assignee: Modern Controls, Inc., Minneapolis, Minn.

[21] Appl. No.: 259,868

[22] Filed: Jun. 15, 1994

[51] Int. Cl.⁶ .............................................. G01N 27/26
[52] U.S. Cl. ..................................... 204/431; 204/432
[58] Field of Search ................ 204/431, 432, 435, 406

[56] References Cited

U.S. PATENT DOCUMENTS

| | | | |
|---|---|---|---|
| 3,223,597 | 12/1965 | Hersch | 204/1 |
| 4,973,395 | 11/1990 | Mayer et al. | 204/406 |
| 5,139,638 | 8/1992 | Mayer | 204/424 |
| 5,184,392 | 2/1993 | Mayer | 29/592.1 |

Primary Examiner—John Niebling
Assistant Examiner—Bruce Bell
Attorney, Agent, or Firm—Palmatier, Sjoquist & Helget

[57] ABSTRACT

An oxygen sensor constructed as a coulometric sensor and capable of detecting oxygen concentrations in the range of 1% or greater concentrations. The coulometric sensor utilizes a gas flow path which has a predetermined section constructed with oxygen-permeable tubing, wherein a portion of the oxygen flowing through the gas flow path will permeate into the sensor to generate an electric current flow indicative of the permeating oxygen level. The length of the tubing section which is constructed from oxygen-permeable material maybe selectively adjusted to control the relative attenuation of oxygen flow through the sensor.

11 Claims, 1 Drawing Sheet

HIGH PERMEABILITY RATE OXYGEN SENSOR

BACKGROUND OF THE INVENTION

The present invention relates to oxygen sensors and more particularly to an oxygen sensor for measuring the oxygen content of a gas containing relatively high levels of oxygen. The invention is used primarily in connection with instruments for measuring the permeability of films and membranes, wherein oxygen is passed into a chamber, one wall of which is enclosed by a material membrane, and a second chamber on the other side of the membrane is coupled to the sensor. Oxygen which permeates through the membrane is detected by the sensor, which generates an electrical signal proportional to the quantity of oxygen detected.

An oxygen sensor of the type generally related to the present invention is disclosed in U.S. Pat. No. 3,223,597, issued Dec. 14, 1965, to Hersch. The Hersch patent discloses a general construction of an oxygen sensor and shows a plurality of layers of materials which are or may be utilized to construct a workable sensor. The principles of the Hersch invention are further elaborated in a construction disclosed in U.S. Pat. No. 4,085,024, issued Apr. 18, 1978, to Lawson. The Lawson patent discloses a particular construction and method of making the oxygen sensor, utilizing many of the same materials which are the subject of the present invention. A further construction of an oxygen sensor of the general type is shown in U.S. Pat. Nos. 5,139,638, issued Aug. 18, 1992, and 5,184,392, issued Feb. 9, 1993, and owned by the assignee of the present invention. These patents disclose improvements in construction which are utilized in connection with the present invention; particularly, improvements to the manufacturing steps which assure a uniform and continuous surface area contact between a cathode and anode via an electrolyte-retentive material wrapped around the anode.

Sensors of the above-described type generally utilize nickel cadmium (Ni-Cd) cathode elements in order to provide a highly sensitive device which can detect oxygen at levels down to parts per trillion. The device is essentially a Ni-Cd battery which is constructed in a manner so that oxygen levels determine the output current. For every oxygen molecule four electrons are released in a Faraday-type electrochemical reaction. As such, the electrodes are immersed in an electrolyte and a gas is passed through the device wherein the current that is generated by the electrodes is equal to the charge-per-second generated by the release of the four electrons per oxygen molecule.

In normal usage, this sensor is used to detect low oxygen contents in dry gas streams at flow rates of 5–50 cubic centimeters per minute (cc/min). The lifetime of the sensor is affected by the gas stream, which tends to dry the electrode as well as dissipate the original charge in the device. At a flow rate of approximately 20 cc/min, a typical sensor of the foregoing type dries out in about 300–400 hours of usage. This drying-out problem was addressed in U.S. Pat. No. 5,139,638 which added a humidifying element to the sensor construction.

The normal charge on sensors of this general type is 800–1,000 milliamp-hours (ma-hrs), at oxygen levels of up to 210 parts per million; at lower oxygen levels the charge has a lifetime in the range of 2,000–20,000 hours. Stated in percentage, this represents the normal lifetime range of a sensor detecting oxygen concentrations of about 0.02 percent. As the percentage oxygen concentration increases, the charge dissipates rapidly; for example, at a 1 percent oxygen concentration and a flow rate of 20 cc/min, the charge lifetime decreases to less than 20 hours. It is, therefore, apparent that sensors of the general type disclosed in the prior art are not suitable for detecting high oxygen concentration levels for any reasonable time period.

A number of modern barrier materials used in the packaging industry are designed to intentionally pass relatively high oxygen concentration levels. Such barriers are useful in packaging fresh fruits and vegetables and other products having a need to "breathe" during the time the product is in transition from packaging to consumption. These new breathable barrier materials permit an extended shelf life for such products before product quality is adversely affected.

SUMMARY OF THE INVENTION

The present invention comprises an oxygen sensor capable of measuring permeability of relatively porous barrier material; i.e., barrier materials having a relatively high permeability to oxygen. A coulometric sensor is modified by constructing a gas flow passage through the sensor, which gas flow passage has a controlled permeability. The test gas is passed through this passage and is conveyed through the sensor via the passage, wherein the controlled permeability of the passage permits a predetermined percentage of the oxygen contained within the gas to permeate through the passage into the coulometric sensor itself. The oxygen escaping through the permeable passage causes the sensor to operate as a conventional coulometric sensor, but the electrical output signal produced by the sensor must be modified to account for the fact that only a percentage of the oxygen in the gas flow produced the electrical signal. The invention includes a nonpermeable tube constructed into the interior of the sensor, a section of permeable tubing connected to the nonpermeable tube and a further nonpermeable tube connected to the permeable section and then to the exterior of the sensor.

It is a principal object of the present invention to provide a coulometric sensor which is capable of measuring high oxygen contents in various gases.

It is another object of the present invention to provide a coulometric sensor for measuring high oxygen concentrations and which has an extended life comparable to the prior art coulometric sensors.

It is another object of the present invention to provide a high oxygen concentration sensor which can provide a calibrated attenuation of the oxygen concentration passing from the gas flow passage to the coulometric sensor.

The foregoing and other objects and advantages will become apparent from the following specification and claims and with reference to the appended drawings.

DESCRIPTION OF THE PREFERRED EMBODIMENT

Figure 1:
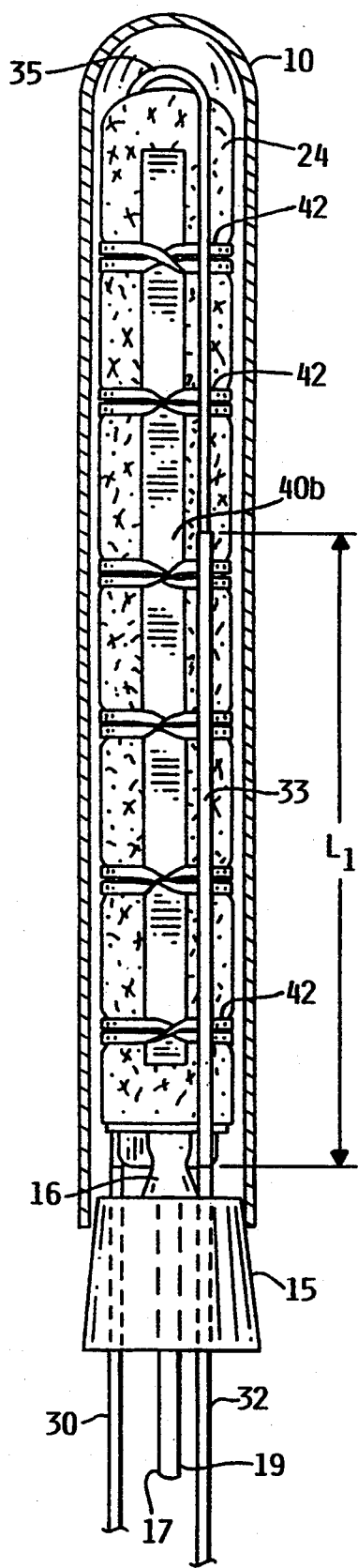
FIG. 1 shows a front cross-sectional view of a coulometric sensor of the present invention.
Figure 2:
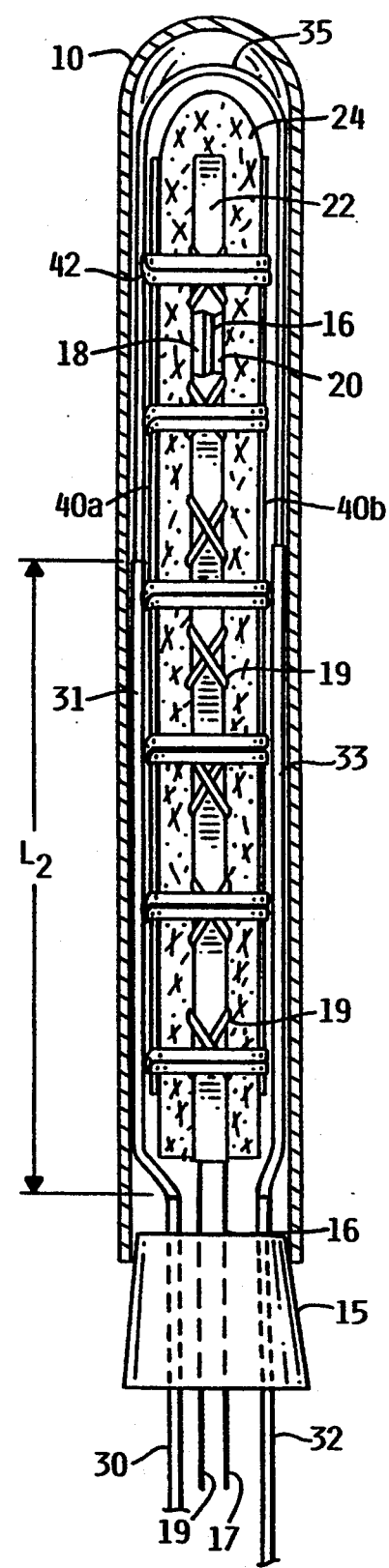
FIG. 2 shows a right side cross-section view of the same sensor.

The invention is shown with reference to FIGS. 1 and 2, wherein respective elevation views in cross section are shown, the view of FIG. 2 being orthogonal to the view of FIG. 1. The interior of the sensor comprises a metallic blade 16 which is overlaid on each of its surfaces by an anode material 18. Blade 16 is preferably a stainless steel flat metallic element, and anode materials 18, 20 are preferably formed of cadmium. A porous insulator material 22 is wrapped and overlaid over the blade and anode materials, and the insulator material is wrapped with a wire 19; one end of the wire 19 is brought out through the interior of the cell for external wiring connection. A cathode material 24 is overlaid over the insulator 22 and is held in relatively flat contact with the insulator material 22 by means of elastic bands 42 and insulating support struts 40a and 40b. Support struts 40a, 40b may be made from plastic or other materials which are impervious to the chemical reactions which occur inside the glass tube 10. A rubber stopper 15 sealably closes the open end of glass tube 10, and a wire 17 is brought out to the exterior of the cell through the stopper 15. One end of wire 17 is securely and electrically connected to the anode blade 16. A pair of capillary tubes 30, 32 are inserted through stopper 15 into the interior of the cell, and each of the capillary tubes are connected to a section of plastic tubing 31, 33 in the interior of glass tube 10. For example, capillary tube 30 is connected to a section of plastic tubing 31 which has a length dimension $L_2$; the other end of plastic tubing 31 is connected to a further capillary tube 35 which extends into the interior of glass tube 10, is bent into a curve proximate the interior end of glass tube 10 and is returned along the other side of the cell to connect with a section of plastic tubing 33. Plastic tubing 33 may have a length of $L_1$, and its other end is connected to the interior end of tube 32. In all cases, the connections between plastic tubing 31, 33 and the respective capillary tubes 30, 32, 35 are sealably made so that no leakage can occur through the connection point.

Plastic tubing 31, 33 is typically formed of Teflon polytetrafluoroethylene or other permeable plastic material selected for its relatively high permeability to oxygen. In other words, a certain percentage of the oxygen which flows through the interior of these plastic tubing sections will permeate through the tubing into the interior of glass tube 10, and this oxygen will cause a coulometric reaction to occur in the cell to thereby generate a current flow between wires 17 and 19.

The respective tubing lengths $L_1$ and $L_2$ may be selected to control the relative attenuation of the oxygen levels permitted to enter into the glass tube 10. Relatively short lengths of tubing will permit only a limited amount of oxygen permeation into the interior of glass tube 10, where as relatively long lengths of tubing 31, 33 will permit a significantly greater permeation of oxygen into glass tube 10. The material Teflon ® is preferably selected for tubing 31, 33 because it permits a relatively high rate of oxygen permeation through its walls, while restricting water permeation to a very negligible extent. This extends the useful lifetime of the sensor by the selective attenuation of oxygen permeation, as well as by preventing excess water from permeating out of the sensor.

In operation, the sensor is first calibrated with a gas containing a known level of oxygen concentration. The electrical wires 17, 19 are connected to a predetermined resistance, and the gas containing the known level of oxygen concentration is passed through the sensor. The detected oxygen permeation will cause a current to flow through the electrical conductors and will therefore cause a voltage drop across the resistor which can be measured, and can be referred to as a calibration voltage ($V_{cal}$). Next, a gas having an unknown oxygen concentration level is passed through the sensor and the voltage drop across the resistance is again measured, as a result of the unknown oxygen concentration ($O_x$). This measured voltage is identified as $V_x$, and the unknown percentage oxygen may then be calculated as follows:

$$O_x = O_{cal} V_x / V_{cal}$$

The foregoing measurements should be corrected to standard temperature and pressure from whatever temperature and pressure exists at the sensor. This correction yields an accurate indication of the unknown oxygen concentration level, based upon the known concentration level and the measured voltages.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An oxygen sensor for connection to a source of gas for measuring the oxygen content in said gas, comprising:
    a) an enclosed container having an interior volume inside container walls;
    b) an anode and cathode in said interior volume, and electrical connections to said anode and cathode, and wires extending from said connections to the exterior of said container, passing through said container walls and sealed therein;
    c) a pair of capillary tubes passing through said container walls and sealed therein, each of said tubes having an open first end in said interior volume and an open second end on the exterior of said container;
    d) at least one length of oxygen-permeable tubing having an end connected to at least one of said open first ends, and means for connecting the other end of said tubing to the other of said open first ends, said tubing extending proximate at least a portion of said anode and cathode; and
    e) means for connecting the open second end of one of said pair of capillary tubes to said source of gas.

2. The sensor of claim 1, wherein said oxygen-permeable tubing comprises two lengths, each length having an end connected to one of said open first ends.

3. The sensor of claim 2, wherein said means for connecting the other end of said tubing further comprises a section of capillary tubing connected between respective other ends of said two lengths.

4. The sensor of claim 3, wherein said oxygen permeable tubing further comprises polytetrafluoroethylene tubing.

5. The sensor of claim 4, wherein said two lengths respectively extend proximate at least a portion of said anode and cathode.

6. The sensor of claim 5, wherein said anode and cathode are positioned in said interior volume intermediate said two lengths.

7. An oxygen sensor for connection to a source of gas for measuring the oxygen content of said gas, comprising:

a) a container having a closed end and an open end;
b) a plug affixed in said open end and sealed therein;
c) an anode and cathode in said container, and electrical wires respectively connected to said anode and cathode and passing through said plug and sealed therein;
d) first and second metallic tubes passing through said plug and sealed therein, each tube having a first open end in said container and a second open end outside said container;
e) at least one length of oxygen-permeable tubing in said container connected between respective first open ends of said metallic tubes; and f) means for coupling one of said metallic tube second open ends to said source of gas.

8. The sensor of claim 7, wherein said at least one length further comprises two lengths of oxygen-permeable tubing.

9. The sensor of claim 8, further comprising a third metallic tube in said container and connected between respective ends of said two lengths of tubing.

10. The sensor of claim 9, wherein said two lengths of tubing are respectively positioned proximate at least a portion of said anode and cathode.

11. The sensor of claim 10, wherein said oxygen-permeable tubing further comprises polytetrafluoroethylene tubing.

* * * * *